United States Patent
Dorn et al.

(10) Patent No.: US 8,447,746 B2
(45) Date of Patent: May 21, 2013

(54) METHODS AND PROGRAM PRODUCT FOR ENABLING DATA RECORDS TO BE LOCATED

(75) Inventors: Karlheinz Dorn, Kalchreuth (DE); Andrew John Hewett, Erlangen (DE); Vladyslav Ukis, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 145 days.

(21) Appl. No.: 12/715,663

(22) Filed: Mar. 2, 2010

(65) Prior Publication Data

US 2010/0228769 A1     Sep. 9, 2010

(30) Foreign Application Priority Data

Mar. 4, 2009    (DE) .................... 10 2009 011 644

(51) Int. Cl.
*G06F 17/30* (2006.01)

(52) U.S. Cl.
USPC .......................................... 707/705

(58) Field of Classification Search
USPC ....................................... 707/705
See application file for complete search history.

(56) References Cited

U.S. PATENT DOCUMENTS

| | | | | |
|---|---|---|---|---|
| 6,476,833 B1 * | 11/2002 | Moshfeghi | ................... | 715/854 |
| 6,507,837 B1 * | 1/2003 | De La Huerga | ...................... | 1/1 |
| 2009/0216993 A1 * | 8/2009 | Venkumahanti et al. | ..... | 711/206 |

* cited by examiner

*Primary Examiner* — Hung Q Pham
(74) *Attorney, Agent, or Firm* — Harness, Dickey & Pierce, P.L.C.

(57) ABSTRACT

In large medical facilities such as hospitals or group practices run by physicians individual patients are often examined and treated by a number of specialists in succession. In view of this it is important, in spite of great differences in the workflows of the individual medical facilities, to coordinate the work of said specialists by way of an operator control device having a uniform user interface. According to at least one embodiment of the invention, methods and a program product for enabling data records to be located are provided for that purpose. By way of the methods and/or the program product, in at least one embodiment a basic page and at least one content page are provided, wherein by use of the basic page at least one display field for presenting information extracted from a data record can be generated on a screen display and wherein by use of the content page, information extracted from a data record can be displayed in a display field.

19 Claims, 2 Drawing Sheets

US 8,447,746 B2

METHODS AND PROGRAM PRODUCT FOR ENABLING DATA RECORDS TO BE LOCATED

PRIORITY STATEMENT

The present application hereby claims priority under 35 U.S.C. §119 on German patent application number DE 10 2009 011 644.3 filed Mar. 4, 2009, the entire contents of which are hereby incorporated herein by reference.

FIELD

At least one embodiment of the invention generally relates to a method for generating a program which enables data records to be located. At least one embodiment of the invention also generally relates to a method for enabling data records to be located. Finally at least one embodiment of the invention generally relates to a corresponding computer program product. What is understood by a data record within the scope of embodiments of the present invention is in particular a data record containing patient data.

BACKGROUND

In large medical facilities such as hospitals or group practices run by physicians individual patients are often examined and treated by a number of specialists in succession. For example it may be necessary for the purposes of a treatment first to have X-rays prepared by a radiologist, whereupon subsequently a treating physician will make a medical diagnosis on the basis of said X-rays.

In order to enable the work of a plurality of specialists to be coordinated it is sometimes the practice nowadays in a medical facility to provide computer workstations at which the specialists are presented with an onscreen display of lists containing activities which they have to carry out on a particular working day for example. A list for a specialist is generated based on a review of patient data records in order to determine whether, for example, new image data relating to said patients has been stored which it is necessary for the specialist to evaluate. If this is the case, the name of the patient and an activity that is to be performed for this patient are included in the list. The programs for automatically generating such lists are often developed specially for individual departments in a medical facility so that specific features in the workflows in the respective department can be taken into account.

For developers of organization programs of the aforesaid kind it is particularly labor-intensive and time-consuming to provide the programs for different departments, since only rarely can parts of an already developed organization program be reused. This makes programs for medical institutions very expensive in terms of both initial procurement and maintenance.

Furthermore it is also necessary for a specialist who alternates between two departments always to be instructed in the operation and use of the respective organization program.

In conjunction with the organization program individual specialists must also use further utility routines in order to be able to complete an activity assigned to them. For example, in order to produce a diagnosis a physician must first search in a data network by way of a file browser in order to locate the image data which a radiologist, for example, generated the day before. Then he/she must have the X-ray images displayed by means of an image viewing program. By way of a further program he/she must finally document the produced diagnostic findings in a written record. Providing this multiplicity of programs implies a high level of expenditure when it comes to equipping a department with computer workstations at which all activities arising in the department can be accomplished. The training of the specialists is also commensurately costly and time-consuming.

Since individual specialists carry out their activities at different computer workstations, tracking down image data can also present problems. In particular in the case of an interdepartmental coordination of activities, when for example a separate department for radiology is present in a hospital, it may be necessary in certain circumstances for a specialist to search for image data relating to a particular patient on different data servers.

In connection with the production of slide presentations it is known from the computer program product PowerPoint® of the company Microsoft® to create, for a plurality of presentation slides that are to have a uniform layout and a common slide frame, each slide in each case from at least two sub-slides. Here, the frame is determined using a sub-slide designated as the master page. Also present on a master page are free fields. These fields are then filled with content via at least one further sub-slide, called a presentation page. Slide presentations having a uniform look-and-feel can then be produced by always using the same master page and different presentation pages.

SUMMARY

In at least one embodiment of the invention a way of locating, with the aid of an operator control device, patient data that fulfills a predefined criterion is provided. In the case of the operator control device it is important to be able to change and extend the possibilities of searching for the data on the basis of the criterion and of accessing the data with less effort. At the same time, however, the operator control device should provide a uniform operating environment.

The method according to at least one embodiment of the invention for enabling data records to be located comprises the steps of:

loading a program code package for a basic page into a working memory of a computer, wherein by means of the basic page at least one display field for presenting information extracted from a data record can be generated on a screen display, loading at least one program code package for a content page into the working memory, wherein by means of the content page information extracted from a data record can be displayed in a display field, initiating the execution of program code of the basic page.

By way of the method of at least one embodiment a plurality of program code packages are combined with one another for the purpose of enabling data records to be located. Toward that end the program code packages are first loaded into the working memory (RAM—Random Access Memory) of a computer. A program code package in this case can comprise one or more files. Next, program code of one of the program code packages is executed by the computer, thereby generating a basic page on the screen display. The data records to be located are preferably data records of patients whose examination or treatment requires an activity to be performed by a specific specialist.

The basic page has display fields in which information can be displayed by means of program code of at least one further program code package. A program code package of this type for displaying information is referred to in this context as a content page.

By way of a display field the basic page simply controls whether and where information appears on the screen display. The actual content of a display field is determined by a corresponding content page. By replacing the content page it is therefore possible to specify which information will be displayed. In this case the different pieces of information will always appear at the same location on the screen display. This advantageously creates a uniform operating environment.

Basic pages and content pages are preferably provided as independent files in which the corresponding program code is stored. If, for example, it is desired to create a new means of compiling information from data records of patients into a list of activities to be performed for a department of a medical facility in a new form, it is only necessary to develop one program code package for a corresponding content page. In particular there is no need to develop a complete new organization program, since an already existing basic page can be used for generating the required display field in which the new content page will present information in a new form. This advantageously reduces the time and costs involved in the development of a new operator control device.

Using a plurality of separate program code packages therefore yields the advantage that individual program code packages can be reused when the method is to be adapted to fit workflows of a different department.

Combining the individual program code packages in the working memory of the computer is preferably accomplished such that during the loading of a program code package into memory a memory address is first stored which describes where in the working memory of the computer the program code package is stored. This memory address is then communicated to the other program code packages. By this means a program code package can calculate a memory address of program code inside a different program code package and on the basis of said calculated memory address initiate an execution of said program code. This means in particular that the individual program code packages do not have to be complete programs which can run independently in a computer.

The method according to at least one embodiment of the invention for enabling data records to be located is advantageously developed by means of the following steps of:
 receiving an input by way of the basic page in order to specify at least one criterion for a search,
 searching for data records in at least one storage medium by means of the basic page, wherein the data records satisfy the at least one criterion for the search,
 displaying information from data records found during the search in a display field by means of a content page.

This yields the advantage of enabling lists containing activities that are to be performed to be generated automatically by way of the method. By specifying search criteria it is possible for example to identify all those patient data records for which an activity is to be carried out by a particular specialist.

The input can be communicated to the basic page for example at the start of the execution of the program code of the basic page. This means that the list of activities that are to be performed can always be generated when a specialist logs in at a computer workstation by way of a password input and an organization program is formed through application of the method according to at least one embodiment of the invention. It can, however, also be provided to allow the search criteria to be specified by an operator by way of a search mask.

Further processing of the search results can advantageously be enabled in at least one embodiment by way of the following steps of:
 receiving an input for specifying a selection of one of the found data records by means of the content page,
 communicating the selection to the basic page,
 ascertaining and displaying information concerning which image data is available in relation to the selected data record in a further display field with the aid of a further content page.

For an operator this provides a simple means of control for an organization program in order to access the image data that exists in relation to a patient data record and that is often stored on special data servers. This yields the advantage that the operator is no longer obliged to track down the image data himself/herself.

A further advantage is afforded, in at least one embodiment, here by way of the following steps of:
 receiving an input for specifying a selection from the available image data by means of the further content page,
 starting an image viewing program for presenting the selected image data on the screen display, wherein the image viewing program is launched by means of the basic page or the further content page.

The operator can therefore select specific image data from the available image data, i.e. for example recorded images of a particular type, simply by way of one input. A suitable viewing program will then be launched automatically. This yields the advantage that the operator only needs to be familiar with the operation of a single program, which is to say the organization program of the kind that results from the method according to the invention, in order to be able to carry out all the activities that are to be performed.

In the step of receiving an input in order to specify the at least one criterion, an advantageous development of the method according to at least one embodiment of the invention is produced if said step comprises the following sub-steps of:
 generating at least one input field by way of the basic page,
 reading in an input by an operator by way of the at least one input field.

This advantageously enables an operator to influence the search and for example to have displayed onscreen only specific activities that are to be performed.

In connection with the search a further advantage is produced if the search for data records is performed in at least two storage media simultaneously. This enables the data records that are to be located with the aid of the search criteria to be found particularly quickly.

Also included within the scope of at least one embodiment of the invention is a method for generating a program for locating data records, comprising the steps of:
 providing a program code package for a program for loading a program code package for a basic page and at least one program code package for a content page into a working memory of a computer, wherein by way of the basic page at least one display field for presenting information extracted from a data record can be generated on a screen display and wherein by means of the content page information extracted from a data record can be displayed in a display field,
 providing at least one program code package for a basic page and at least one program code package for a content page,
 consolidating all the program code packages in a computer-readable form on at least one storage medium.

The provided program code packages can in each case consist of one or more files. Source code or binary code already in computer-readable form can be contained therein.

The term "consolidating" is preferably understood to mean storing, linking and storing, and possibly also compiling, linking and storing.

For developers of an organization program the method affords the advantage that only a small part of the overall program actually needs to be reprogrammed in order to adapt an existing program to the requirements of a particular customer. Specifically, it is only necessary to develop one further program code package for a content page, which package will display the information in accordance with the customer's wishes.

The method is advantageously developed if there is provided in addition a selection of a basic page and at least one content page on the basis of which the program for loading loads program code packages for the selected basic page and the at least one selected content page.

This produces the advantage that a program code package for a content page can also be particularly easily integrated into the program when the program is already being used in a hospital for example. The program code package for the new content page can then be simply added to the already present program code packages. If the new content page is then selected, the information displayed by the new content page is also available in a corresponding display field.

Advantageously the selection is passed to the program for loading by means of a file in an XML format (XML —Extensible Markup Language). Such a file is also easily readable for an operator and can be adapted by the operator without a special programming environment. In other words an operator can generate a new organization program quite simply by modifying the file. Provided all the selected program code packages for the basic page and the content pages are already present in computer-readable form, no further working step is necessary.

Developing a new version of a program that enables data records to be located is thus possible in a particularly easy way. All the program code packages can be prepared and from these an organization program individually tailored for a customer for example can then be generated by providing a file containing a selection of specific program code packages.

Instead of using a file it is, however, also possible to integrate a content page into the program while the program is already running. This can happen in that a program code package for the content page is loaded as a module into the working memory by the program.

The method is also advantageously developed if by providing a selection it is specified which information will be displayed in a display field by way of the at least one content page. In this case the selection is preferably stored in a file in an XML format.

Enabling the information to be selected results in many cases in the advantage that an organization program for a customer can be particularly easily tailored to the customer's requirements. For this it is often sufficient namely to specify in the case of an already fully developed content page which information from found data records will actually be displayed.

In connection with the at least one program code package for a content page an advantageous development is produced if said package has at least one separate program code module by which a reading-in or processing of data records by the computer is effected when an execution of the same is initiated.

In other words at least two strictly separate program code modules are contained in a program code package for a content page: the module for displaying the information in a display field and the module for reading in or processing data records. Creating the program code package from separate program code modules results in the advantage that the program code modules can be developed and improved independently of one another.

This advantage can be achieved for a program code package for a basic page in comparable fashion if the at least one program code package for a basic page has at least one separate program code module by means of which, when an execution of the same is initiated, a search for or reading-in or processing of data records is effected by the computer.

Also included within the scope of at least one embodiment of the invention is a computer program product having at least one computer-readable data medium, wherein the following are stored on the at least one computer-readable data medium:

a program code which is embodied for loading program code for a basic page and for initiating an execution of said program code as well as for loading program code for at least one content page, wherein by way of the basic page at least one display field for presenting information extracted from a data record can be generated on a screen display and wherein by way of the content page information extracted from a data record can be displayed in a display field, a program code which is embodied for providing at least one basic page, a program code which is embodied for providing at least one content page.

By way of this computer program product a generic program is provided for locating data records. By selecting a basic page and at least one content page it is namely easily possible for a user to generate a program tailored to his/her requirements.

BRIEF DESCRIPTION OF THE DRAWINGS

The invention is explained in more detail below with reference to example embodiments, in which.

DETAILED DESCRIPTION OF THE EXAMPLE EMBODIMENTS

Figure 1:
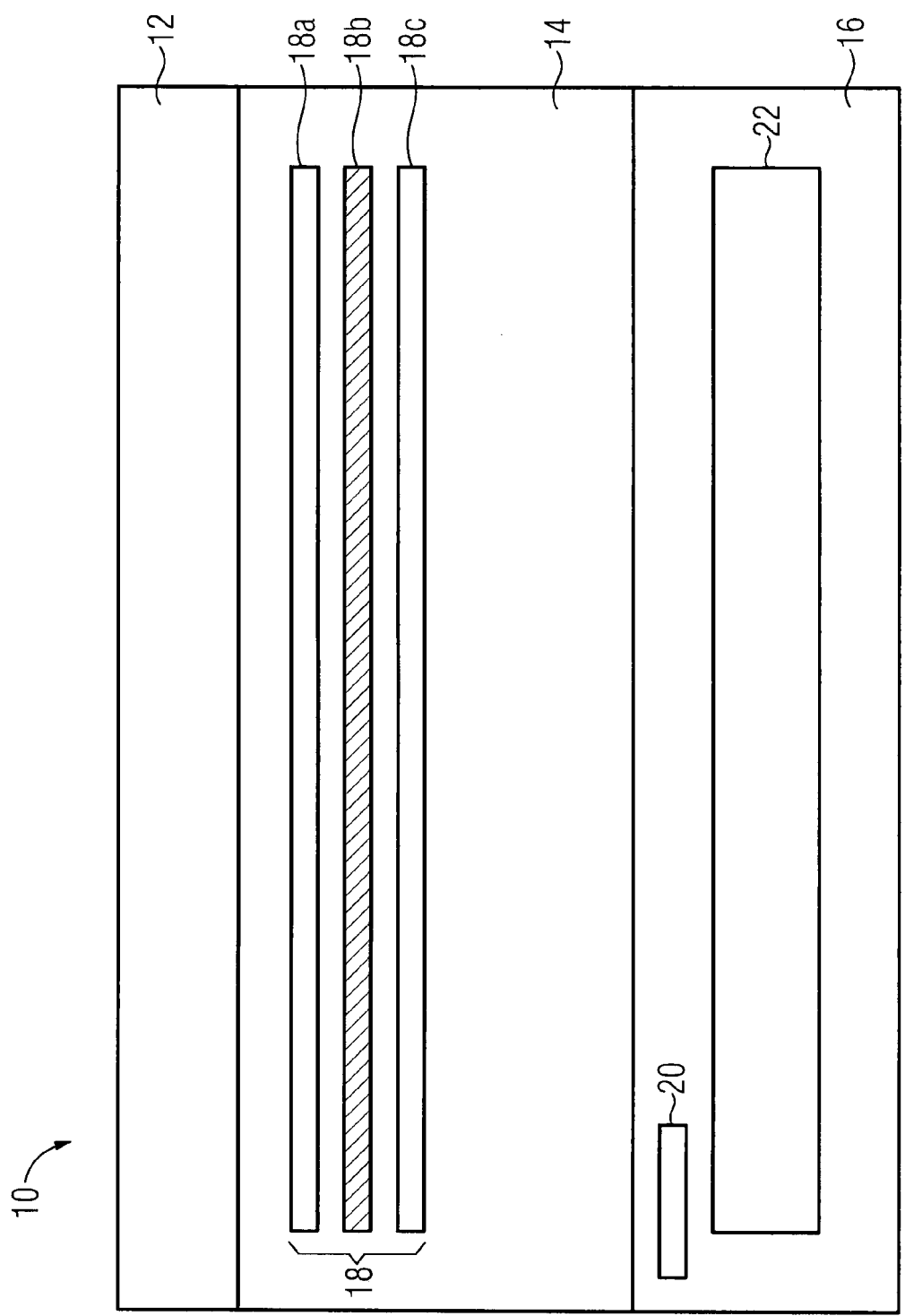
FIG. 1 shows a schematic representation of a user interface on a screen display, as generated by way of an embodiment variant of the method according to the invention for enabling data records to be located.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

A user interface 10 shown in FIG. 1 is displayed on a screen (not shown in further detail in FIG. 1) of a computer in a hospital. The user interface 10 is generated by an organization program of the hospital. By way of the organization program it is possible for a physician to receive an onscreen display providing a list of all those patients for whom he/she is to produce a diagnosis. By way of the organization program he/she can, however, also access the image data generated for example by a technologist for the purpose of producing a diagnosis.

The organization program was formed at the time of the launching of same by a load program from a plurality of separate program code packages. For that purpose the load program loaded the program code packages into a working memory of the computer. Which program code packages are loaded into the working memory by the load program is specified by way of a file which is read by the load program when the latter is started.

A first program code package is a program code package for a basic page by means of which a selection bar 12 of the user interface 10 is generated on the screen. By means of program code of the basic page it is effected to that end that such memory contents are specified accordingly in a graphics memory of the computer via which colors of pixels of the screen are controlled as a function of contents of corresponding memory cells of the graphics memory. In this case the memory contents are chosen such that the selection bar 12 of the basic page is represented on the user interface 10. Only outlines of the selection bar 12 are shown in FIG. 1.

Two display fields 14, 16 have also been predefined on the user interface 10 by the basic page. In this case, however, the display fields 14, 16, as managed by the basic page itself, are simply two areas in the graphics memory which the basic page can make available to another program code package for the purpose of presenting graphical content.

A list 18 made up of working instructions 18a to 18c is displayed in the display field 14.

In the display field 16 there are a name field 20 and a patient table 22 which provides an overview of recorded medical images of the patient whose name is displayed in the name field 20.

The list 18 was not generated in the display field 14 by program code of the basic page. Instead it belongs to a second of the program code packages from which the organization program was created. The second program code package forms a content page by means of which there are listed in the display field 14 all those patients for whom at the time of the execution of the organization program and generation of the user interface 10 recorded images were present with the aid of which the physician is to produce a diagnosis.

The individual patients are listed in the form of working instructions 18a to 18c, each of which contains the name of the patient and further data relating to the diagnosis (this information is not shown in FIG. 1). Which information is displayed in a working instruction 18a to 18c is determined by means of specifications in a file which was read in by the load program at the time the latter was started.

The information for generating the working instructions 18a to 18c is extracted from patient data records. For that purpose there is provided in the program code package of the content page program code which, prior to a generation of the list 18 on the user interface 10, causes the information from patient data records to be read out. The patient data records are, however, stored in an area in the working memory provided by the basic page.

The patient data records are stored in an area in the working memory that is provided by the basic page because the task of ascertaining the right patient data records is performed by program code of the basic page. In order to ascertain patient data records the program code of the basic page initiates a search for patient data records in a plurality of database servers.

The criteria for the search for the patient data records were communicated to the basic page indirectly by way of a different program at the start of the organization program. Examples of such criteria are whether the physician having identified himself/herself by way of a password during the login and currently using the organization program is responsible for a particular patient whose data is stored in a patient data record in question, and whether recorded images of the patient are present.

By way of the selection bar 12 the physician can, however, also specify other search criteria by means of which he/she can cause the data relating to other patients to be found.

In order to initiate the search the program code of the basic page causes the computer to generate signals which are transmitted by way of a connection cable of a data network to one of the database servers in each case. The criteria according to which the search is to be conducted in each database server are communicated by way of the signals. The signals are transmitted to the different database servers in immediate succession so that the search will run in all the database servers in parallel, in other words simultaneously.

The found patient data records are transmitted by the individual database servers by way of the connection cable to the computer in the form of suitable signals. The program code of the basic page thereupon causes the received data to be stored in the area in the working memory provided therefor by the basic page, where they can then be read by the content page.

The program code for initiating the search and storing the patient data records represents an independent program code module which may have been developed by developers independently of the rest of the program code of the basic page.

In order to obtain more precise information on one of the displayed working instructions 18a to 18c, a physician selects the corresponding working instruction 18a to 18c. In the example shown in FIG. 1 this is the working instruction 18b. For the selection the physician makes use of a computer mouse (not shown in FIG. 1) to move a pointer on the user interface 10 into an area assigned to the working instruction 18b for the purpose of receiving an input. This area is marked by way of hatching in FIG. 1. A comparable input device can also be used instead of a computer mouse. The working instruction 18b includes (not shown in FIG. 1) the name of the patient and a description of a study that is to be conducted, in this instance "Examination relating to a fractured femur".

By generating a signal via buttons of the computer mouse while the pointer is located in the area of the working instruction 18b, the physician causes an execution of the program code of the content page to be initiated. By way of the program code it is initially effected that on the basis of the patient data record associated with the working instruction 18b it is determined which working steps specifically have to be carried out by the physician in order to fulfill the task displayed in the working instruction 18b. For that purpose the program code of the content page resorts to schemes of useful sequences of working steps that are stored in the program code package of the content page. In the case of the example shown in FIG. 1 a scheme containing working steps for a basic diagnosis has been accessed in relation to the working instruction 18b. However, a physician can also specify a different scheme by means of a menu which can be generated in the display field 14 by the content page.

It is also ascertained with the aid of the scheme which recorded images are necessary for processing the working steps. In the example shown in FIG. 1 the following are specified as working steps for producing the basic diagnosis in relation to the selected working instruction 18b: "Diagnosis based on an X-ray" and "Diagnosis based on photographs of contusions".

An execution of program code of the basic page is then initiated by the program code of the content page. The program code of the basic page in turn causes program code of a third program code package of the organization program to be executed. The third program code package provides a second content page by which the name field 20 containing the patient name, as also displayed in the working instruction 18b, and the patient table 22 are presented in the display field 16. Corresponding memory contents in the graphics memory are specified for the visualization by means of the program code of the content page.

The individual working steps from the scheme (not shown in FIG. 1) are presented in the patient table 22. A description for the associated recorded image (likewise not shown in FIG. 1) is also displayed for each working step. In the case of the above example there thus appears (not shown in FIG. 1) in relation to the first working step a description "X-ray of femur, left", and in relation to the second working step a description for a whole set of recorded images: "Photographs of femur, frontal and lateral".

When the physician selects a working step by way of the computer mouse, program code of the second content page in turn causes an execution of corresponding program code of the basic page to be initiated. By way of the latter it is ascertained, with the aid of the patient data record, on which data server of the data network the recorded image resides which is required for carrying out the working step.

Next, similarly to the search for patient data records, the computer causes signals to be generated which are transmitted by way of the connection cable to the data servers and as a result data from files in which the recorded images are stored is transferred to the computer. An example of a data server is an NAS (Network Attached Storage), from which data can be received via the data network.

The receiving of the data from a data server is made possible by a separate program code module of the basic page. It can, however, also be effected by the basic page, by way of program code of a further program code module, that image data from files residing on a hard disk of the computer itself will be read.

Finally it is ascertained by way of the basic page with the aid of the received data, with which image viewing program the recorded images can be presented on the screen display in a suitable manner in order, for example, to produce a diagnosis. The identified image viewing program is thereupon launched, thereby resulting in the recorded image appearing on the screen display. The physician can then carry out the working step. Thus, with regard to the already cited first working step (diagnosis based on an X-ray), an image viewing program for X-rays is accordingly launched and the recorded image with the description "X-ray of femur, left" is displayed on the screen display.

By selecting the next working step displayed in the patient table 22 the physician can then have the next recorded image displayed on the screen display. In the example this is therefore the working step "diagnosis based on photographs". To that end the physician sees displayed onscreen the photographs from the set of images with the description "photographs of femur, frontal and lateral views".

It is thus possible for the physician, by using a single program, namely the organization program itself, to work through all of the working steps on the patient table 22. The physician repeats this procedure for each of the remaining working instructions 18a to 18c of the list 18.

The program code for visualizing the list 18 and for detecting an input by means of a computer mouse is formed from separate program code modules of the content page. As a result it is possible for developers to tailor the appearance of the list and the use of the content page e.g. to customer wishes without in the process influencing the processing of the patient data records by the rest of the program code of the content page. The same applies to the program code for visualizing the name field 20 and the patient table 22, which program code forms separate program modules of the program code package of the second content page. The selection bar 12 of the basic page is also generated by a separate program code module of the program code package of the basic page.

Figure 2:
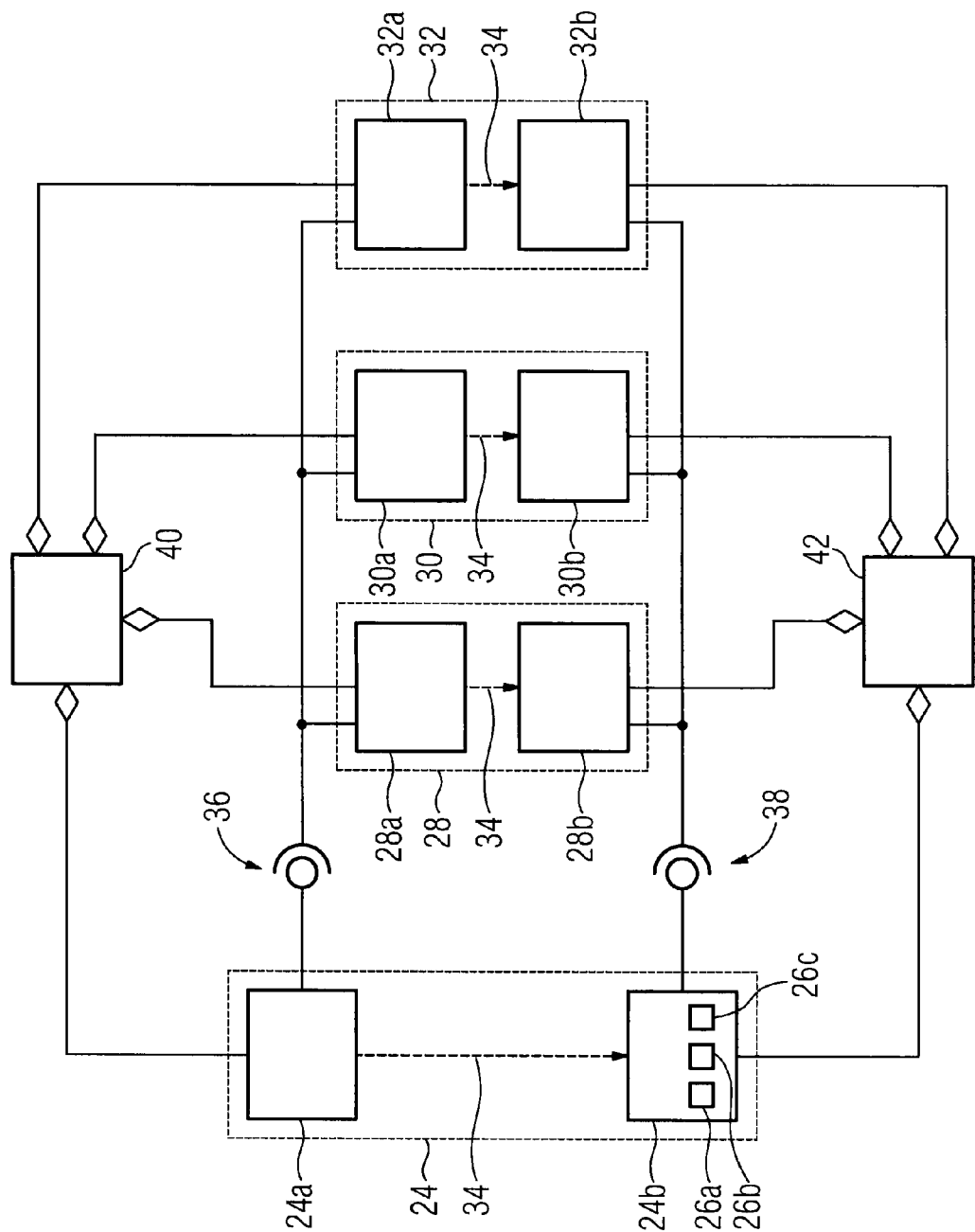
FIG. 2 shows a schematic representation of program code packages of a load program and further program code packages loaded by said program into a working memory of a computer, wherein the program code packages collectively form an embodiment variant of a computer program product according to the invention.

With regard to the organization program described in connection with FIG. 1, FIG. 2 shows those program code packages that have been loaded into the working memory of the computer by the load program. Also shown are program code packages of the load program itself.

FIG. 2 symbolically illustrates that each of the program code packages which make up the component parts of the organization program are in each case composed of two program sections. These are described in more detail below. Each of the program sections may have been developed separately by developers of the computer program product.

The selection bar 12 shown in FIG. 1 is part of a program code which in FIG. 2 forms a first program section of the basic page, specifically a so-called frontend 24a of the basic page. Overall, the frontend 24a comprises that program code by means of which graphical elements of the basic page are presented on the user interface 10 shown in FIG. 1. In other words it encompasses the program code that modifies memory contents of the graphics memory of the computer. The program code of the frontend 24a also receives signals from the computer mouse or a keyboard of the computer when, for example, a user specifies search criteria in the selection bar 12 shown in FIG. 1.

The remainder of the program code of the basic page is contained in the other program section of the basic page. This part of the program code package for the basic page forms a so-called backend 24b of the basic page. This program code comprises all the program code modules that cause the computer to search for or read in or process data records. Contained in the backend 24b in particular are the program code module 26a described in connection with FIG. 1, by which the search for patient data can be initiated, the program code module 26b for receiving data from the data network, and the program code module 26c for driving the controller of the hard disk of the computer.

The list 18 shown in FIG. 1 in the display field 14 is also generated by way of independently developed program code, namely the program code package 28 of the content page for working instructions. This is also subdivided into a frontend 28a and a backend 28b. As in the case of the basic page, the program code for generating graphical elements on the screen display is contained in the frontend 28a. The frontend 28a also accepts signals from the computer mouse and the keyboard when said signals are generated in connection with one of the working instructions 18a to 18c.

In addition to the actual presentation of the list 18 shown in FIG. 1 in the display field 14 on the screen display, however, other processing steps also have to be performed by the content page 18. For example, the schemes for determining the individual working steps explained in connection with FIG. 1 must be administered. This is handled by the backend 28b of the content page 28.

It is also shown in FIG. 2 that in addition to the content page 28 for the list 18 of the working instructions 18a to 18c shown in FIG. 1, the computer program product also includes a two-part program code package comprising a frontend 30a and a backend 30b of the content page 30 for the patient table 22 and the name field 20 described in connection with FIG. 1.

Finally there is also a program code package for a content page 32, via which a user is given the possibility to store patient data on a separate data medium or to import patient data from such a medium into the data network. This program code package is also subdivided into a frontend 32a and a backend 32b. In the situation shown in FIG. 1 no display field is assigned to the content page 32, so no graphical elements of the content page 32 can be seen on the user interface 10 shown in FIG. 1.

As already explained in relation to the frontends 24a and 28a, the frontends 30a and 32a each contain only that program code by means of which a graphical user interface (GUI) of the organization program is provided.

In the case of the frontends 24a, 28a, 30a, 32a the program code modules—described in connection with FIG. 1 but not shown in more detail in FIG. 2—for presenting graphical elements, which are in fact accommodated in the frontends 24a, 28a, 30a, 32a, exchange data with program code modules of the backends 24b, 28b, 30b, 32b, likewise not shown in further detail, via communication channels 34. A communication channel 34 is a logical structure which is provided by way of functions in the program code packages. Thus, in order for example to activate, by means of a program code module of a frontend which has received a signal from a computer mouse, a functionality of the organization program by means of a corresponding program code module of a backend, a suitable function of the program code module of the backend will be invoked by the program code module of the frontend. Calling the function causes program code that forms the function and is part of the program code module of the backend to execute, as a result of which, for example, data is processed in a desired manner.

The display fields 14, 16 shown in FIG. 1 are assigned by the frontend 24a of the basic page 24 to the frontends 28a, 30a, 32a by way of a call to an activation function of the corresponding frontend 28a, 30a, 32a. This form of action by means of which the frontend 24a exerts influence on the frontends 28a, 30a, 32a is symbolized in FIG. 2 by way of a software interface 36.

As a result of the activation function being invoked, program code of the corresponding frontend of the content page is executed, thereby initially causing the position and size of an assigned display field, designated by reference signs 14 and 16 in FIG. 1, to be read out from an area of the working memory. The position and size were determined by means of the basic page. The storing of the position and size in the area of the working memory is also handled by the basic page.

The graphical representations of data from the patient data records are then displayed on the user interface 10 shown in FIG. 1 in accordance with the assigned positions and sizes. The graphical representations form the visible elements, which is to say, for example, the list 18 or the patient table 22. For the purposes of the visualization, corresponding memory contents in the graphics memory are specified by means of program code of the frontend of the content page.

As in the case of the activation functions, the backend 24b of the basic page can pass the position of patient data records stored in the working memory of the computer to the backends 28b, 30b, 32b of the content pages 28, 30, 32 likewise via a call to a function. This too is symbolized in FIG. 2 by way of a software interface 38.

Like the program code packages of the basic page 24 and of the content pages 28, 30, 32, the program code package of the load program itself also has two program sections. Memory addresses which specify a location of the frontend 24a of the basic page 24 and of the respective frontends 28a, 30a, 32a of the content pages 28, 30, 32 in the working memory of the computer are stored by way of a first program section, a management unit 40. The memory addresses can be requested from the management unit 40 by the other frontends in each case, such that e.g. the frontend 24a of the basic page 24 can invoke the activation functions of the frontends 28a, 30a, 32a of the content pages 28, 30, 32.

A second management unit 42 of the load program correspondingly manages the memory addresses of the backends 24b, 28b, 30b, 32b and provides the memory addresses as necessary.

By way of the example explained with reference to FIG. 1 and FIG. 2 it is shown how workflows between a plurality of specialists in a hospital can be coordinated by way of an organization program according to an embodiment variant of the inventive computer program product. At the beginning of a working day a physician can have the activities that he/she has to carry out presented to him/her in an onscreen display on a computer workstation by means of the organization program. At the same time all the necessary working steps are displayed to him/her by means of the same program. In addition the physician can access patient data and image data. This means that the physician can process all the working steps without personally having to launch a further program. By building the organization program out of a basic page and a plurality of content pages it is possible to provide computer workstations across all departments in the hospital with a standardized user interface, though one in which the presentation of content can nonetheless be tailor-made for each department.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE SIGNS
10 User interface
12 Selection bar
14, 16 Display field
18 List
18a, 18b, 18c Working instruction
20 Name field
22 Patient table
24 Basic page
24a, 28a, 30a, 32a Frontend
24b, 28b, 30b, 32b Backend
26a, 26b, 26c Program code module
28, 30, 32 Content page
34 Communication channel 36, 38 Software interface
40, 42 Management unit

What is claimed is:

1. A method for enabling data records to be located, comprising:
   loading a basic page file into a working memory of a computer based on instructions of a loading configuration file, the basic page file providing a program code package for a basic page;
   loading at least one content page file into the working memory based on instructions of the loading configuration file, each of the at least one content page files providing a program code package for a content page
   initiating execution of program code of the program code package for the basic page;
   generating, on a screen display, at least one display field based on the basic page file; and
   displaying, in the at least one display field based on the basic page file, information extracted from a data record, the loading the at least one content page file including,
      storing a package memory address of the program code package for the content page,
      communicating the package memory address to the program code package for the basic page,
      calculating a function memory address of at least one program code function of the program code package for the content page, and
      initiating, from within the program code package for the basic page, execution of the at least one program code function.

2. The method as claimed in claim 1, further comprising:
   receiving an input by use of the basic page in order to specify at least one criterion for a search,
   searching for data records in at least one storage medium by use of the basic page, wherein the data records satisfy the at least one criterion for the search, and
   displaying information from data records found during the search in a display field by use of a content page.

3. The method as claimed in claim 2, further comprising:
   receiving an input for specifying a selection of one of the found data records by use of the content page,
   communicating the selection to the basic page, and
   ascertaining and displaying information concerning which image data is available in relation to the selected data record in a further display field with the aid of a further content page.

4. The method as claimed in claim 3, further comprising:
   receiving an input for specifying a selection from the available image data by use of the further content page, and
   starting an image viewing program for presenting the selected image data on the screen display, wherein the image viewing program is launched by use of the basic page or the further content page.

5. The method as claimed in claim 2, wherein the receiving of an input for specifying the at least one criterion comprises:
   generating at least one input field by use of the basic page,
   reading in an input by an operator by way of the at least one input field.

6. The method as claimed in claim 5, wherein the search for data records is performed in at least two storage media simultaneously.

7. The method as claimed in claim 2, wherein the search for data records is performed in at least two storage media simultaneously.

8. The method of claim 1, further comprising:
   storing a package memory address of a first program code package;
   communicating the package memory address to a second program code package;
   calculating a function memory address of at least one program code function of the first program code package; and
   initiating, from within the second program code package, execution of the at least one program code function based on the calculated function memory address.

9. The method of claim 1, wherein
   the basic page file includes binary code loadable into the working memory and executable on the computer, and
   the content page includes binary code loadable into the working memory and executable on the computer.

10. A computer readable medium including program segments for, when executed on a computer device, causing the computer device to implement the method of claim 1.

11. A method for generating a program for the purpose of locating data records, comprising:
    providing a program code package for a program for loading, into a working memory of a computer based on instructions of a loading configuration file, a basic page file and at least one content page file, the basic page file providing a program code package for a basic page, and the at least one content page file providing a program code package for a content page;
    providing the at least one basic page file and the at least one content page file;
    consolidating the provided program code packages in a computer-readable form on at least one storage medium;
    providing the loading configuration file, the loading configuration file specifying a selection of a basic page and at least one content page on the basis of which the program for loading loads program code packages for the selected basic page and the at least one selected content page;
    generating, on a screen display, at least one display field based on the basic page file; and
    displaying, in the at least one display field based on the at least one content page file, information extracted from a data record, the loading the at least one content page file including,
       storing a package memory address of the program code package for the content page,
       communicating the package memory address to the program code package for the basic page,
       calculating a function memory address of at least one program code function of the program code package for the content page, and
       initiating, from within the program code package for the basic page, execution of the at least one program code function.

12. The method as claimed in claim 11 wherein the loading configuration file is in an XML format.

13. The method as claimed in claim 11, wherein by providing a selection, it is specified which information will be displayed in a display field by use of the at least one content page.

14. The method as claimed in claim 11, wherein the at least one program code package for a content page has at least one separate program code module by which a reading-in or processing of data records by the computer is effected when an execution of the same is initiated.

15. The method as claimed in claim 11, wherein the at least one program code package for a basic page includes at least one separate program code module by which, when an execution of the same is initiated, a search for or reading-in or processing of data records is effected by the computer.

16. The method of claim 11, further comprising:
  storing a package memory address of a first program code package;
  communicating the package memory address to a second program code package;
  calculating a function memory address of at least one program code function of the first program code package; and
  initiating, from within the second program code package, execution of the at least one program code function.

17. The method of claim 11, wherein
  the basic page file includes binary code loadable into the working memory and executable on the computer, and
  the content page includes binary code loadable into the working memory and executable on the computer.

18. A computer program product having at least one computer-readable data medium, wherein at least the following is stored on the at least one computer-readable data medium:
  a first program code configured to,
    load a basic page file providing a second program code for a basic page,
    initiate execution of the second program code, and
    load at least one content page file, each of the at least one content page file including content page program code for a content page;
    the basic page file;
    the at least one content page file; and
  at least one loading specification file for specifying at least one content page and at least one basic page to be loaded by the first program code, wherein
    at least one display field is generated on a screen display based on the basic page file, and
    information extracted from a data record is displayed in the at least one display field based on the at least one content page file, the loading the content page file including,
      storing a package memory address of the program code package for the content page,
      communicating the package memory address to the program code package for the basic page,
      calculating a function memory address of at least one program code function of the program code package for the content page, and
      initiating, from within the program code package for the basic page, execution of the at least one program code function.

19. The computer program product of claim 18, wherein the computer program product is further configured to:
  store a package memory address of a first program code package;
  communicate the package memory address to a second program code package;
  calculate a function memory address of at least one program code function of the first program code package; and
  initiate, from within the second program code package, execution of the at least one program code function.

* * * * *